United States Patent [19]

Lennon et al.

[11] Patent Number: 4,999,163
[45] Date of Patent: Mar. 12, 1991

[54] DISPOSABLE, PRE-PACKAGED DEVICE FOR CONDUCTING IMMUNOASSAY PROCEDURES

[75] Inventors: Donald J. Lennon, Hopedale; Timothy C. Murphy, Jr., Westwood, both of Mass.

[73] Assignee: Hygeia Sciences, Inc., Newton, Mass.

[21] Appl. No.: 404,061

[22] Filed: Sep. 8, 1989

Related U.S. Application Data

[63] Continuation of Ser. No. 107,240, Oct. 29, 1987, abandoned.

[51] Int. Cl.$^5$ ...................... G01N 21/00; G01N 31/22
[52] U.S. Cl. ........................................ 422/58; 422/56; 422/60; 422/69; 422/101; 422/102; 436/541; 436/810
[58] Field of Search ................. 436/541, 810; 422/60, 422/69, 101, 102, 56, 58

[56] References Cited

U.S. PATENT DOCUMENTS

| Re. 30,267 | 5/1980 | Bruschi | 23/230 |
|---|---|---|---|
| 3,811,840 | 5/1974 | Bauer et al. | 23/253 TP |
| 3,825,410 | 7/1974 | Bagshawe | 23/230 R |
| 3,849,256 | 11/1974 | Linder | 422/102 |
| 3,888,629 | 6/1975 | Bagshawe | 436/541 |
| 3,909,363 | 9/1975 | Bucalo | 195/103.5 R |
| 4,033,723 | 7/1977 | Givner et al. | 436/810 |
| 4,125,376 | 11/1978 | Razulis | 422/56 |
| 4,246,339 | 1/1981 | Cole et al. | 435/7 |
| 4,248,355 | 2/1981 | Kolb et al. | 215/274 |
| 4,254,082 | 3/1981 | Schick et al. | 422/61 |
| 4,256,694 | 3/1981 | McAllister et al. | 422/58 |
| 4,340,479 | 7/1982 | Pall | 210/490 |
| 4,366,241 | 12/1982 | Tom et al. | 435/7 |
| 4,407,943 | 10/1983 | Cole et al. | 435/7 |
| 4,409,182 | 10/1983 | Macklem | 422/61 |
| 4,425,438 | 1/1984 | Bauman et al. | 436/541 |
| 4,549,655 | 10/1985 | Forsythe, Jr. et al. | 206/569 |
| 4,594,223 | 6/1986 | Dyke et al. | 422/56 |
| 4,623,461 | 11/1986 | Hossome et al. | 201/445 |
| 4,632,901 | 12/1986 | Valkirs et al. | 435/5 |
| 4,727,019 | 2/1988 | Valkirs et al. | 435/5 |
| 4,729,875 | 3/1988 | Chandler | 422/60 |

FOREIGN PATENT DOCUMENTS

PCT/US85/-
00870  3/1985  PCT Int'l Appl. .

Primary Examiner—Robert J. Warden
Assistant Examiner—Lyle Alfandary-Alexander
Attorney, Agent, or Firm—Staas & Halsey

[57] ABSTRACT

A disposable, pre-packaged device for conducting an immunoassay procedure that results in the production of separable liquid and solid phases. The device includes a cup having an inlet and presenting a liquid phase receiving chamber. An absorbent for liquid phase materials is in the chamber and a series of ribs hold the absorbent away from the walls of the chamber providing a breathing space extending around the absorbent. A porous capture media element for capturing and displaying solid phase products of the procedure is disposed adjacent the inlet of the device in fluid communication with the absorbent so that in operation the absorbent promotes flow of liquid phase through the capture element. A lid element is mounted on the cup adjacent the inlet and the lid and the cup are held together by welding of annular flanges. The lid element includes an elongated cylindrical member extending through the inlet and defining a throat for directing flow of liquid phase onto the capture media. The cylindrical member has an annular surface at its inner end for contacting the porous capture media and holding it in tight fluid communication with the absorbent. A vent hole is provided in the lid flange to facilitate venting of the breathing space. The vent hole and the throat opening are disposed in a single plane so that a single planar coil element may be used to keep out contamination during storage and shipment.

18 Claims, 1 Drawing Sheet

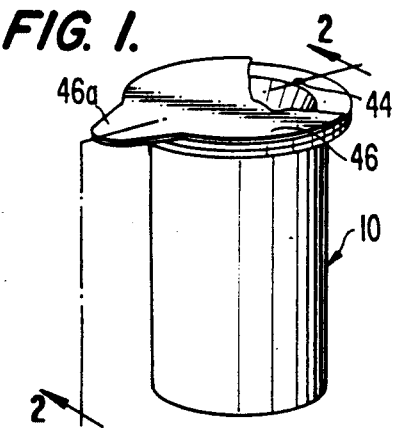
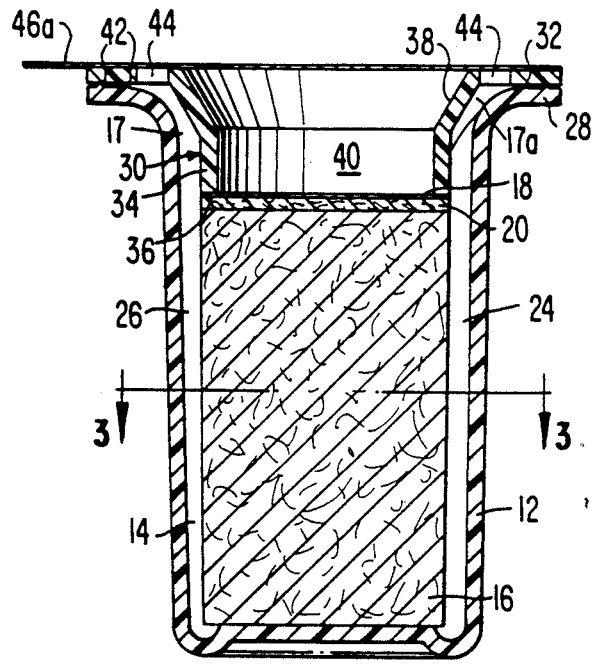
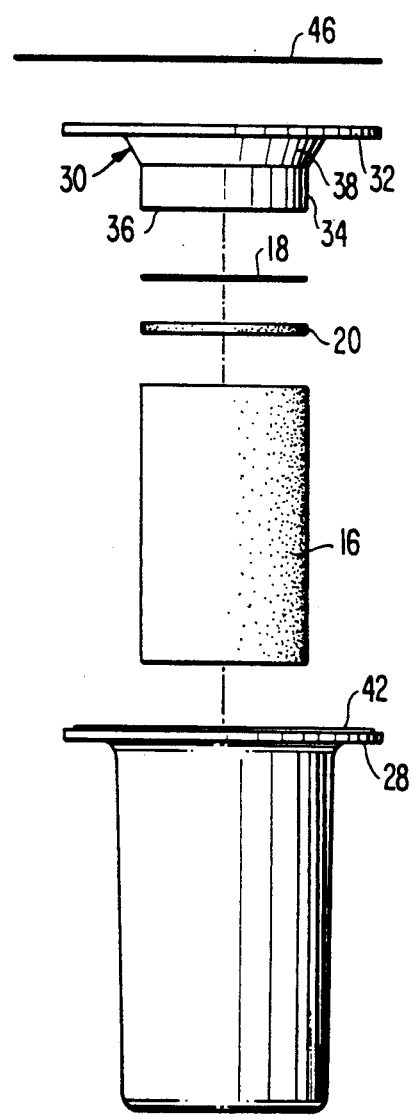
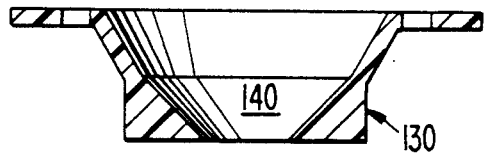
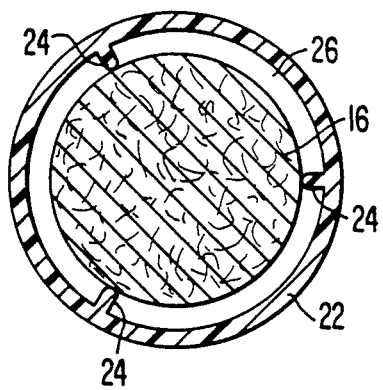

DISPOSABLE, PRE-PACKAGED DEVICE FOR CONDUCTING IMMUNOASSAY PROCEDURES

This is a continuation of copending application Ser. No. 07/107,240 filed on Oct. 29, 1987 now abandoned.

BACKGROUND OF THE INVENTION

1. Field of the Invention

The present invention related to device for conducting immunoassay procedures. In particular, the invention relates to disposable, pre-packaged devices which are particularly suitable for conduct of diagnostic procedures based on immunological reactions at remote sites such as physician's offices and homes of users.

2. Description of the Prior Art

Since the important discovery of Millstein and Kohler reported in *Nature* 256: 495-497, 1975, the development of highly sensitive and specific immunoassay procedures has proceeded at a rapid pace. In fields such as clinical medicine, forensic sciences, environmental quality testing, food quality assurance, drug testing and other related areas, it has become possible to determine the presence and/or amount of trace substances in test samples even when such substances are present in very low concentrations in the order of parts per million, or even less. The development of non-radioactive labels or markers, such as enzyme color formers, has facilitated the use of immunoassay diagnostic procedures outside of laboratory settings and in remote sites such as physician's offices and even the homes of the users. In the physician's office, immunological procedures are useful to provide rapid, simple assays which may be performed while the patient is still in the office so that the diagnosis can be accomplished without delay and treatment instituted during a single visit. Without such simple assays, it has often been necessary for the physician to collect a sample from the patient during a first visit and to have the sample analyzed by a clinical laboratory with the results reported back to the physician by the laboratory at a later time. In the meanwhile, the patient was sent home and was required to return for a second visit with the physician in order to receive appropriate treatment and/or medication. Manifestly, such delay was inefficient and inappropriate and in some cases could even be life threatening.

Home testing has became desirable to facilitate testing by the consumer in the privacy of his or her own home. The results of such testing might, for example, indicate the necessity or lack of necessity of a visit to the physician. Examples of useful test for the "at home" market include tests for pregnancy, ovulation, streptococcus infection and other infections which are detectable by analysis of urine, saliva or other appropriate test samples.

For remote site testing, assuming appropriate sensitivity and specificity can be achieved, there are at least three other requirements for practical assay procedures. The first of these desirable factors is speed in that the assay must be performed in an acceptably short period of time, the shorter the better. Stability is also a desirable feature in that the components of the assay should be stable for an extended period of time without refrigeration or special handling and the assay results or readouts should be sufficiently stable so that the interpretation may be confirmed even several days after the initial test is performed. Finally, from a commercial view point it is desirable that the test be as simple as possible requiring only minimal or no instrumentation and precluding mistakes and poor performance resulting in incorrect interpretations.

Immunoassay kits employing enzyme markers are presently commercially available today for determining pregnancy and ovulation in the physician's office and in the home of the user. The technical components generally required in such kits are (1) a solid phase bearing immobilized antibody, (2) an enzyme labelled antibody, (3) a rinse solution (in some cases this may be the users tap water), and (4) a substrate for the enzyme. A typical procedure is that the sample is mixed with the solid phase and incubated (with or without a subsequent rinse step) and then the sample is discarded, the solid phase is then contacted with the enzyme labelled antibody and incubated. Thereafter the solid phase is rinsed and contacted by the substrate. After a period of time (ca 5 minutes) the color of the solid phase is observed. One such assay is described in U.S. Letters Pat. No. 4,632,901.

Enzyme labelled immunoassays are not without their own drawbacks resulting from the instability of some enzyme systems, the number of kit components and the complexity of the procedure. Such shortcomings have been addressed in the co-pending application of Cole, Davis and Sigillo, entitled "Metal Sol Capture Immunoassay Procedure, Kit For Use Therewith and Captured Metal Containing Composite," and filed Oct. 7, 1987, (serial number not yet assigned), which application is assigned to the assignee of the present application. In said co-pending Cole et al. application, a metal particle label is utilized and a collectible, solid phase, metal containing composite is formed. The composite is collected on a filter element or the like where the presence of analyte in the original sample is determined or detected by evaluating, through direct visual examination, the presence of metal in the collected solid phase composite.

One of the difficulties encountered in the development of test devices for remote site testing is the provision of a practical pre-packaged disposable device to facilitate efficient, relatively inexpensive test procedures. This, of course, requires a device which is inexpensive to construct, which has a shelf life appropriate to the commercial use of the device, which is protected against contamination during handling, and which may be simply and readily utilized when the appropriate time arises. The device illustrated in the '901 patent mentioned above addresses some of these problems and is available commercially; however, the device has a number of deficiencies including retarded flow of fluid into the absorbent. It is believed that such flow problems were perhaps alleviated to some degree by the provision of notched vertical venting grooves in the periphery of the absorbent plug. Such venting grooves facilitated venting of the device during use through small ports provided near the bottom of the container. Of course, liquid could escape through such vent ports creating a messy operation, sealing prior to use was difficult and the manufacture of the grooved absorbent plugs is a relatively expensive operation.

Other prior single test devices are illustrated in U.S. Letters Pat. Nos. 4,366,241 and 4,623,461. However, these devices are of limited application and also have excessive complexity.

SUMMARY OF THE INVENTION

The present invention provides relief from many of the shortcomings of the prior art devices described above. In this regard, the invention provides a simplified, pre-packaged, disposable test device wherein the liquid sample flows freely through a porous capture media means where products of the procedure are captured and displayed. The device comprises structural elements which facilitate assembly, pre-packaging and sealing of the device prior to intended use.

In accordance with the present invention, a disposable, prepackaged device for conducting an immunoassay procedure is provided. The device comprises cup means defining a chamber for receiving liquid residues from the procedure. The cup means includes structure defining a liquid inlet communicating with the chamber. Absorbent means are disposed in the chamber for promoting flow of liquid into the chamber and spacer means are provided in the chamber for holding the absorbent means away from the inner walls of the chamber to present a breathing space communicating with the inlet. The breathing space extends essentially entirely around the absorbent means to facilitate venting and thus flow of fluid into the absorbent during the conduct of the test procedure. The device preferably includes porous capture media means for capturing and displaying products of the procedure, such porous capture media means being disposed adjacent the inlet of the device and in fluid communication with the absorbent means. Additionally, the device preferably includes a lid element including means defining a throat disposed to extend through the inlet of the cup means for directing flow of liquid assay reaction media through the inlet and onto the porous capture capture means.

To facilitate manufacture and assembly of the device, the lid element preferably includes means defining a pusher member for contacting the porous capture media means and pushing the latter toward the absorbent means and into fluid communication therewith. Also, to facilitate assembly the device preferably includes an annular flange on the lid element extending around the throat and a mating, corresponding annular flange on the cup means extending around the inlet Means are provided for securing the flanges together in mated relationship with the throat aligned with the inlet.

To further facilitate pre-packaging of the device, the lid element flange includes means defining at least one vent hole disposed in fluid communication with the breathing space of the cup device and facilitating venting of the latter to the atmosphere. Such construction enables the use of a removable sealing means closing the throat and the vent hole to thereby prevent introduction of foreign material into the device prior to its intended use. In this regard, in a preferred embodiment of the invention the external openings of the vent hole and of the throat are disposed in the same plane and the sealing means comprises a single planar element, such as a piece of metal foil, disposed in sealing relationship to the openings.

In a most desirable commercial form of the invention, the device includes a lid element mounted on the cup means adjacent the inlet and having a centrally disposed cylindrical member extending through the inlet and defining a throat positioned for directing flow of liquid assay medium through the inlet and onto the capture media means. The cylindrical member has an annular surface at its free end disposed for contacting the porous capture media means and pushing the latter toward the absorbent means and into said fluid communication. In this form of the invention, the lid element also includes an annular flange extending around the cylindrical element and the cup means includes a mating, corresponding annular flange extending around the inlet. Means are provided for securing the flanges together in mated relationship with the throat aligned with the inlet and with the annular surface disposed in pushing relationship relative to the capture means.

In one preferred form of the invention, the porous capture media means comprises a filter element having pores of a size to prevent passage of desired reaction products. In another preferred form of the invention, the porous capture media means comprises a microporous membrane to which is bound an immunoreactive substance that is specifically reactive in the desired reaction. In either case, the device preferably includes a hydrophobic, porous separator element interposed between the porous capture media means and the absorbent means to insure complete separation between the captured reaction product on the capture media means and the liquid phase which has been drawn into the absorbent means.

In a particularly preferred form of the invention, the cup means comprises a generally cylindrical wall surrounding the chamber, the absorbent means comprises an elongated element which is generally circular in cross-sectional configuration, and the spacer means comprises a plurality of generally rectangularly shaped wing members extending radially inwardly from the cylindrical wall of the cup means.

BRIEF DESCRIPTION OF THE DRAWINGS

FIG. 1 is an isometric view of a disposable, pre-packaged device for conducting an immunoassay procedure, which device embodies the principles and concepts of the present invention;

FIG. 2 is a cross-sectional view taken along view line 2—2 of FIG. 1;

FIG. 3 is a cross-sectional view of the device of the invention taken along view line 3—3 of FIG. 2;

FIG. 4 is an elevational, exploded view of the device illustrating the relationship between the various components of the assembled device; and FIG. 5 is a cross-sectional view of an alternative form of the lid element useful in connection with an alternative device embodying the invention.

DETAILED DESCRIPTION OF THE INVENTION

The concepts and principles of the present invention are embodied in a disposable, pre-packaged device 10 which is useful for conducting an immunoassay procedure. The type of procedure utilized is not important for purposes of the present invention other than that the device may be used to facilitate any sort of procedure which results in the production of a collectible phase which incorporates a tag of some sort to indicate a positive or negative test results. Generally speaking, the device 10 of the present invention will be utilized in connection with procedures which employ a visually detectable colored or color forming tag such as an enzyme or metal sol particle tag. However, it is within the perceived usefulness of the invention that the device might well be employed in connection with procedures wherein a reactant is tagged with an instrument detectable tag such as a radioactive isotope, a fluorescent material or a chemiluminescent material.

The device 10, in its preferred form, includes a cup member 12 encompassing a chamber 14 for receiving liquid residues from an immunoassay procedure. Absorbent means in the form of an elongated absorbent plug 16, which is generally circular in cross-sectional configuration, is disposed in chamber 14 for the purpose of promoting flow of liquid into the chamber, as will be explained in more detail hereinbelow. Cup 12 includes structure at its upper end defining a liquid inlet opening 17 that is in fluid communication with the interior of chamber 14.

Device 10 also includes porous capture media means in the form of a circular element 18 for capturing and displaying products of an immunoassay procedure, a function which will be described in greater detailed hereinafter. Element 18 is disposed adjacent inlet opening 17 and operationally is in fluid communication with absorbent plug 16 during the conduct of the immunoassay procedure. A circular, hydrophobic, porous separator element 20 may be interposed between element 18 and absorbent plug 16 to facilitate essentially complete separation of said reaction products and liquid residues. Again, the function and characteristics of separator 20 will be described in greater detail hereinbelow.

Cup 12 comprises a cylindrical wall 22 which surrounds chamber 14. A plurality of elongated, generally rectangular wing members 24 extend radially inwardly from wall 22, as can best be seen in FIG. 3. The innermost edge of each member 24 contacts the outer periphery of absorbent plug 16, and thus, wing members 24 present spacer means disposed in chamber 14 for holding absorbent plug 16 away from the inner surfaces of wall 22 to provide a breathing space 26 which communicates with inlet 17 and extends essentially entirely around the circumferential periphery of absorbent plug 16.

Cup 12 is also provided with an annular flange 28 which extends around inlet 17. Device 10 further includes a generally annular lid element 30 having a mating, corresponding flange 32. Element 30 also comprises a cylindrical member 34 having an annular surface 36 at its free end. A hollow, generally frustoconical segment 38 interconnects cylindrical member 34 and flange 32. Together, cylindrical member 34 and frusto-conical segment 38 present means defining a throat 40 which extends through inlet 17. Functionally, throat 40 is positioned for directing the flow of liquid reaction medium onto the porous capture media element 18.

Flange 28 extends around inlet 17 and flange 32 extends around throat 40. Flanges 28 and 32 are mating, corresponding flanges, and when the device is assembled as illustrated in FIG. 2, annular surface 36 is in tight, pushing contact with respect to porous capture media element 18. In this connection, it is to be understood that absorbent plug 16 is preferably somewhat resilient and compressible, and during assembly surface 36 contacts element 18 and pushes the latter toward absorbent plug 16 and into tight fluid communication therewith by way of the pores of separator element 20.

During assembly, flanges 28 and 32 are held together in mated relationship with throat 40 aligned with inlet 17 and With annular surface 36 held tightly against element 18 in pushing relationship thereto. Accordingly, cylindrical member 34 and its free annular surface 36 present a pusher element disposed in pushing relationship relative to the porous media capture element 18. Manifestly, during assembly, the flanges 28 and 32 are held together by a mechanical device (not illustrated) and while so held together, the same are preferably sonically welded. To facilitate such procedure, means in the nature of annular sonic weld energy director beads 42 are initially provided on flange 28 to facilitate the sonic welding process. However, it is to be understood that sonic welding and beads 42 are not critical aspects of the present invention. And in fact, there are alternative methods for securing flanges 28 and 32 together, such alternative methods being conventionally used and known to those skilled in the art.

A pair of spaced, opposed vent holes 44 are provided in flange 32, as can best be seen in FIG. 2. Vent holes 44 are disposed in fluid communication with breathing space 26 via the annular portion 17a of inlet 17 that surrounds cylindrical member 34 and frusto-conical segment 38 of lid element 30. Vent holes 44 are thus available to facilitate venting of breathing space 26 to the atmosphere surrounding the device 10 during the conduct of an immunoassay procedure utilizing device 10.

As can best be seen viewing FIG. 2, the external openings of vent holes 44 and the external opening of throat 40 are all disposed in a single plane extending along the upper surface of flange 32. Sealing means in the nature of a single planar foil element 46 is removably affixed to the upper surface of flange 32 using conventional adhesive means. Foil element 46 is provided with a conventional tab 46a to facilitate removal of element 46 from the upper surface of flange 32 by peeling. Accordingly, foil element 46 closes throat 40 and vent holes 44 to thereby prevent introduction of foreign material into the device prior to its intended use and yet foil element 46 is readily removable by the user at the time the device 10 is to be used.

Cup 12 and lid element 30 may be constructed of plastic or glass or any other suitable material, and these elements may preferably be made by an injection molding procedure utilizing a thermoplastic material. The only limitation on the materials of construction being that the same must be inert to the reactants and reaction products.

Absorbent plug 16 is an absorbent member having capillary passages extending therethrough in a diversity of directions which are both transverse to and generally parallel to the surfaces at the upper and lower ends of plug 16. There are a number of materials which are well known to those of ordinary skill in the art to which this invention pertains that may be used to construct absorbent plug 16. Such materials include hydrophillic polymers, particulate absorbents, glass fibers, cotton fibers, cellulose fibers, wood pulp and/or sponge. Other materials which may find use as plug 16 include polysaccharides, for example cellulosic materials, such as paper and cellulose acetate. Cellulose acetate fibers arranged in the same manner as in a cigarette filter may be utilized to construct absorbent plug 16. Another useful material is the absorbent material used in a tampon. A particularly useful material is a cellulose acetate fiber Transorb plug as manufactured by American Filtrona Co. In any event, the important features of the materials useful in the construction of plug 16 are simply that the same be capable of absorbing aqueous materials and that they possess sufficient structural integrity to permit the initial construction of the device. Further useful absorbent materials are disclosed, for example, in U.S. Letters Pat. Nos. 4,246,339; 4,623,461; 4,632,901; and 4,366,241.

Separator element 20 simply serves the purpose of separating porous capture media element 18 from absorbent plug 16 to assure that liquid at the upper surface of absorbent plug 16 does not interfere with the results to be evaluated at the surface of element 18. In this respect, separator element 20 should preferably be constructed of a hydrophobic, porous material, such as, for example, the hydrophobic, porous non-woven rayon material disclosed in U.S. Pat. No. 4,246,339 or the porous polyethylene or other material which does not bind receptor non-specifically, such as is disclosed in International Publication No. WO85/05451 (International Application No. PCT/US85/00870). A porous polyester material available commercially in sheet form from Porex Technologies is a particularly useful material. Other useful materials include glass fiber layers (Whatman) and porous plastic layers (Porex or Pellon).

With regard to the porous capture media element 18, this element may take any one of several different forms depending on the type of immunoassay procedure which is utilized. For example, if the immunoassay involves an ELISA technique, element 18 may be a membrane having a co-reactant for the reagent to be assayed in the test liquid sample immobilized on the internal and external surfaces thereof. Such membranes are utilized in the procedures disclosed in U.S. Letters Pat. No. 4,246,339 and in said International Publication no. WO85/05451. The membranes useful in connection with such procedure are fully disclosed and described in U.S. Letters Pat. No. 4,340,479. Manifestly, methods for binding immunoreactants to such membranes are well known to those skilled in the art to which the present invention pertains.

In another form of the invention, the porous capture media element 18 may be composed of such things as glass fiber filters (Whatman GF/A), regenerated cellulosic membranes (Schleicher and Schuell) and microporous membranes (Millipore MF series membranes HAWP, SSWP, SMWP and SCWP with pore sizes of 0.45, 3, 5 and 8 microns respectively). All of these materials have been successfully utilized for capturing and collecting a solid phase product resulting from an immunoassay procedure. In particular such materials have been found useful for capturing the collectible, solid phase, metal containing composite which results from the immunoassay procedure described in said co-pending and co-assigned application of Cole et al. Manifestly, in such process the porous capture media element simply comprises a filter element having pores of a size to prevent passage of desired reaction products. Accordingly, the desired reaction products accummulate on the surface of the element and are available there for visual inspection.

Another capture material which is potentially useful as element 18 is a microporous member to which avidin has been linked whereby biotinylated reaction materials may be captured.

Manifestly, the capture matrices disclosed in said co-pending Cole et al. application are all useful in connection with the present invention, as are the absorbent materials and separator materials disclosed therein. Accordingly, the entirety of the disclosure of said co-pending application of Cole et al. is hereby specifically incorporated herein by reference.

In the operation of device 10, immunoreagents are contacted with a sample and the mixture is allowed to incubate for a period of time, all as is well known to those skilled in the immunoassay art. After a sufficient incubation period, the reaction mixture is simply poured through throat 40 and onto element 18. Capillary action in absorbent plug 16 promotes flow of liquid through element 18 and through separator 20, and thus the liquid phase is separated from the solid phase by element 18. Air or other gases originally present in plug 16 are readily vented through space 26 and upwardly through vent holes 44. This facilitates the absorbent action in absorbent plug 16, since with the structure provided by the present invention, there is no substantial possibility of entrapping air within the device to impede the flow of fluid into absorbent plug 16. To insure complete separation between the liquid phase in absorbent plug 16 and the solid phase on the surface of porous media capture element 18, a rinse solution may be poured through throat 40 after the reaction mixture has been introduced. Manifestly, formation of coloration on the surface of element 18 provides an almost instantaneous indication of the results of the assay, whether the same involves a metal sol tag in accordance with the procedure disclosed in said co-pending Cole et al. application, or an enzyme tag and an immobilized antibody, such as is disclosed in U.S. Letters Pat. No. 4,407,943.

It will be readily apparent to those of ordinary skill in the art, that while the device of the present invention has been described in connection with certain specific immunoassay procedures, the same may also be utilized in connection with other immunoassay procedures that involve a liquid phase reaction and production of a labelled immunoreaction product that is capturable on a porous media capture element, either by a filtration process or chemical linkage. In this regard, element 18 may be a filter element having pores of a size to prevent passage of a desired reaction products, or a porous element, such as a microporous membrane, to which is bound an immunoreactive substance that is specifically reactive in the desired immunoassay reaction.

Sealing element 46 may simply be a formed piece of an impermeable sheet material. Preferably element 46 may be a piece of metal foil which is removably attached by an adhesive to the upper surface of flange 32 in closing relationship to throat 40 and vent holes 44. In this regard, the attachment may preferably be by way of an adhesive material which permits foil 46 to simply be peeled away from the top of device 10 utilizing tab 46a to thereby to expose throat 40 and vent holes 44. While foil 46 remains in place, all internal areas of device 10 are protected against inadvertent introduction of foreign materials. Accordingly, the transportability, shelf life and storability of the device is enhanced.

With reference to FIG. 5, an alternative lid element 130 is illustrated. Lid element 130 is generally the same as lid element 30 except that it is designed so that throat area 140 is frusto-conical in shape. Thus, the liquid flowing through throat 140 is channeled into a much smaller flow area and therefore contacts a much smaller area of porous capture medium 18. This results in a concentration of the tagged reaction product captured on medium 18 and a resultant enhancement of coloration. Lid element 130 may be used to replace lid element 30, particularly in connection with the form of the invention where the porous capture medium 18 is a simple filter and the tag is a metal sol particle as disclosed in said co-pending Cole et al. application.

We claim:

1. A disposable, pre-packaged device for conducting an immunoassay procedure which results in the production of separable liquid and solid phases, said device comprising:

a cup means defining an elongated chamber for receiving the liquid phase from said procedure, said cup means comprising a cylindrical wall extending around said chamber, a closure wall at one end of the chamber and a liquid inlet communicating with the chamber;

a generally cylindrically shaped absorbent plug disposed entirely within the chamber for absorbing said liquid phase, said plug having a lower surface resting on said closure wall, a circumferential peripheral surface extending therearound and an upper flat surface disposed in alignment with said inlet;

a porous capture media means for capturing and displaying a solid phase separated from said liquid phase, said porous capture media means being disposed between said inlet and said flat surface and being in fluid communication with said absorbent plug via said flat surface, whereby said absorbent plug promotes flow of liquid phase through said capture media means during conduct of an immunoassay procedure; and a spacer means in the chamber holding the peripheral surface of the absorbent plug away from the cylindrical wall to thereby present an annular breathing space communicating directly with the peripheral surface of the absorbent plug and extending essentially entirely around said peripheral surface, said cup means including a vent hole adjacent said inlet in communication with said space to facilitate venting of the absorbent plug via said peripheral surface and said space as the plug absorbs a liquid phase.

2. The invention of claim 1, wherein said plug is generally circular in cross-sectional configuration and said spacer means comprises a plurality of general rectangular shaped wing members extending radially inwardly from said cylindrical wall.

3. A device as set forth in claim 1, wherein said porous media means comprises a filter element having pores of a size to prevent passage of desired reaction products.

4. A device as set forth in claim 3, comprising a porous separator element interposed between the porous means and the flat surface of the absorbent plug.

5. A device as set forth in claim 4, wherein said separator element is constructed of a hydrophobic material.

6. A device as set forth in claim 1, wherein said porous media means comprises a microporous membrane to which is bound an immunoreactive substance that is specifically reactive in the desired reaction.

7. A device as set forth in claim 6, comprising a porous separator element interposed between the porous mean and the flat surface of the absorbent plug.

8. A device as set forth in claim 7, wherein said separator element is constructed of a hydrophobic material.

9. A device as set forth in claim 1, comprising a lid element mounted on the cup means adjacent the inlet and having a centrally disposed, elongated cylindrical member extending through the inlet, said element having an opening extending through the cylindrical member for directing flow of liquid assay reaction medium through the inlet and onto the capture means.

10. A device as set forth in claim 9, wherein said lid element includes an annular flange extending around said opening and said cup means includes a mating, corresponding annular flange extending around said inlet, said device including means for securing the flanges together in mated relationship with the opening aligned with the inlet.

11. A device as set forth in claim 10, wherein said vent hole is disposed in said lid element flange.

12. A device as set forth in claim 11, comprising removable sealing means closing the opening and the vent hole to thereby prevent introduction of foreign material into the device prior to intended use.

13. A device as set forth in claim 12, wherein the external portions of the opening and the vent hole are disposed in a common plane and said sealing means comprising a single planar element disposed in sealing relationship to said external portions.

14. A device as set forth in claim 9, wherein said cylindrical member includes a pusher segment for contacting said capture means and exerting a pushing force against the latter to hold the capture means and the plug in said fluid communication.

15. A device as set forth in claim 14, wherein said lid element includes an annular flange extending around said opening, and said cup means includes a mating, corresponding annular flange extending around said inlet, said device including means for securing the flanges together in mated relationship with the opening aligned with the inlet and with the pusher segment disposed in said contacting relationship relative to the capture means.

16. A device as set forth in claim 15, wherein said pusher segment is cylindrical and has an annular surface at its free end disposed for contacting the porous capture media means, said opening extending through the cylindrical pusher segment.

17. A device as set forth in claim 15, wherein said vent hole is disposed in the lid element flange.

18. A device as set forth in claim 17, comprising removable sealing means closing the opening and the vent hole to thereby prevent introduction of foreign material into the device prior to intended use.

* * * * *